United States Patent [19]

Takahashi

[11] Patent Number: 5,531,719

[45] Date of Patent: Jul. 2, 1996

[54] VASCULAR CATHETER WITH HELICAL SPACE

[75] Inventor: Tohru Takahashi, Fujinomiya, Japan

[73] Assignee: Terumo Kabushiki Kaisha, Tokyo, Japan

[21] Appl. No.: 266,553

[22] Filed: Jun. 28, 1994

[30] Foreign Application Priority Data

Jun. 29, 1993 [JP] Japan .................................. 5-159790

[51] Int. Cl.$^6$ ............................................ A61M 25/00
[52] U.S. Cl. ............................................ 604/280; 604/282
[58] Field of Search ................................ 604/204, 280, 604/282; 128/656–658

[56] References Cited

U.S. PATENT DOCUMENTS

| | | | |
|---|---|---|---|
| 3,498,286 | 3/1970 | Polanyi et al. ................ | 604/282 X |
| 3,913,565 | 10/1975 | Kawahara . | |
| 4,100,309 | 8/1977 | Micklus et al. . | |
| 4,385,635 | 5/1981 | Ruiz . | |
| 4,430,083 | 2/1984 | Ganz et al. ................... | 604/283 |
| 4,616,652 | 10/1986 | Simpson ....................... | 128/658 X |
| 4,739,768 | 6/1986 | Engelson . | |
| 4,801,297 | 1/1989 | Mueller . | |
| 4,840,622 | 6/1989 | Hardy .......................... | 604/280 |
| 4,899,787 | 2/1990 | Ouchi et al. .................. | 138/131 |
| 4,955,862 | 9/1990 | Sepettea ....................... | 604/164 |
| 4,998,923 | 3/1991 | Samson et al. . | |
| 5,069,674 | 12/1991 | Fearnot et al. ................ | 604/282 |
| 5,147,315 | 9/1992 | Weber .......................... | 604/164 |
| 5,180,376 | 1/1993 | Fischell ........................ | 604/282 |
| 5,275,152 | 1/1994 | Krauter et al. ................ | 128/4 |
| 5,337,733 | 8/1994 | Baverfeind et al. ........... | 128/4 |
| 5,357,979 | 10/1994 | Imran .......................... | 128/772 |
| 5,380,304 | 1/1995 | Parker .......................... | 604/282 |

FOREIGN PATENT DOCUMENTS

| | | |
|---|---|---|
| 0063859 | 11/1982 | European Pat. Off. . |
| 0102685 | 3/1984 | European Pat. Off. . |
| 0166998 | 1/1986 | European Pat. Off. . |
| 0370785 | 5/1990 | European Pat. Off. . |
| 0437795 | 7/1991 | European Pat. Off. . |
| 0594201 | 4/1994 | European Pat. Off. . |
| 2946385 | 5/1981 | Germany .............. 604/282 |
| 62-17082 | 4/1987 | Japan . |
| 92019308 | 11/1992 | WIPO ................... 604/282 |

OTHER PUBLICATIONS

U.S. Patent Application Serial No. 08/186,563, filed Jan. 26, 1994, "Vascular Dilatation Instrument and Catheter" Attorney docket No. 018961–004, (copy *not* enclosed).

*Primary Examiner*—John D. Yasko
*Assistant Examiner*—Adam J. Cermak
*Attorney, Agent, or Firm*—Burns, Doane, Swecker & Mathis

[57] ABSTRACT

A vascular catheter usable for intravascular surgical operation, highly localized injection of medicine such as anticancer drugs, and angiography.

The main portion of the catheter body is made up of an inner tube formed synthetic-resin and an outer tube formed of a synthetic resin covering the outside surface of the inner tube. The tip of the catheter body is made up of the portion of the outer tube extending from the distal end of the inner tube. The inner tube has one or more grooves, slots or slits formed in the distal end portion.

29 Claims, 8 Drawing Sheets

VASCULAR CATHETER WITH HELICAL SPACE

FIELD OF THE INVENTION

The present invention relates to a vascular catheter used for intravascular surgical operation, highly localized injection of medicine such as anticancer drugs, and angiography.

BACKGROUND OF THE INVENTION

Medical treatment using vascular catheters is developing to smaller and smaller blood vessels as from the heart to the brain. Lesions of the brain blood vessels are aneurysm, arteriovenous malformation (AVM) and dural arteriovenous fistula (DAVF), for example. Demand for a vascular catheter for treating or examining such lesions of blood vessels is more and more increasing.

A vascular catheter for this purpose must be inserted to the intended part of a blood vessel being passed in complicatedly bent or branched blood vessels.

For an intravascular surgical operation called emboluation technique conducted for treating lesions in the brain blood vessels such as aneurysm and arteriovenous malformation, for example, the distal end of a small-diameter vascular catheter is inserted to or near the lesions in the brain. Then, a liquid embolizing material such as cyanoacrylate or dimethylsulfoxide solution of ethylene-vinyl alcohol copolymer, a granular embolizing material such as granules of poly(vinyl alcohol) or a expanding member such as coil is injected from the distal end of the catheter.

For such a small-diameter vascular catheter, high manipulability to insert it easily and quickly up to a target lesion passing in complicatedly bent or branched small blood vessel is required in addition to the chemical and biological safety required for common vascular catheters.

To have high manipulability, a small-diameter vascular catheter must have the following four properties.

The first property is that the catheter can convey the pushing force in the direction of the axis added to the proximal end portion by the operator up to the distal end or has so called pushability.

The second property is that the catheter can convey the turning force around the axis added to the proximal end portion up to the distal end or has so called turnability.

The third property is that the catheter can be advanced in blood vessels along the guide wire inserted beforehand easily and without causing damage to the wall of the blood vessels or has so called pliability.

The fourth property is that the catheter does not kink at bents (curves and crooks) in blood vessels after the guide wire is removed or has reluctance to kinking.

A vascular catheter having a catheter body of the double-tube structure made up of a comparatively rigid inner tube and a comparatively soft and flexible outer tube covering the outside surface of the inner tube and having the distal end portion extending beyond the distal end of the inner tube and forming the tip of the catheter body was developed and currently used.

In more detail, U.S. Pat. No. 4,385,635 discloses a vascular catheter in which the inner tube is formed of polyamide and the outer tube is formed of polyurethane and the distal end portion is tapered so that the inner diameter becomes gradually smaller to the distal end. This catheter has a problem that it kinks easily at the boundary between the two-tube portion and the single tube portion because of the abrupt change of the rigidity at the boundary.

Japanese utility model application published under Publication No. 17082/1987 discloses a vascular catheter which uses the outer tube formed of silicone rubber and the inner tube formed of a hard synthetic resin selected from among polyethylene, polypropylene, fluororesin and hard vinyl chloride. In this catheter, a step of the height equal to the wall thickness of the inner tube is formed in the lumen at the boundary between the two-tube portion and the single tube portion. Because of the step, this catheter kinks easily at the boundary and hence has small reluctance to kinking.

Further, a vascular catheter recently put to practical use which uses the inner tube formed of polypropylene and the outer tube formed of ethylene-vinyl acetate copolymer has also the same problem of small reluctance to kinking.

SUMMARY OF THE INVENTION

The object of this invention is to provide a vascular catheter of a double-tube structure which has improved easiness of insertion, flexibility to bend along a guide wire or blood vessel, reluctance to kink, and manipulability and can be used for small blood vessels.

The vascular catheter of the present invention is a vascular catheter comprising a flexible slender catheter body which is made up of an inner tube formed of a synthetic resin and an outer tube formed of a synthetic resin covering the outside surface of the inner tube and has a lumen, said catheter body has a main portion and a tip portion, the main portion of the catheter body is made up of the inner and outer tubes, the tip of the catheter body is made up of the portion of said outer tube extending from the distal end of the inner tube, and the inner tube has one or more grooves, slots or slits in the distal end portion.

DETAILED DESCRIPTION OF THE PREFERRED EMBODIMENTS

The vascular catheter of the present invention is illustrated below in detail with the preferred embodiments shown in the attached drawings.

Figure 1:
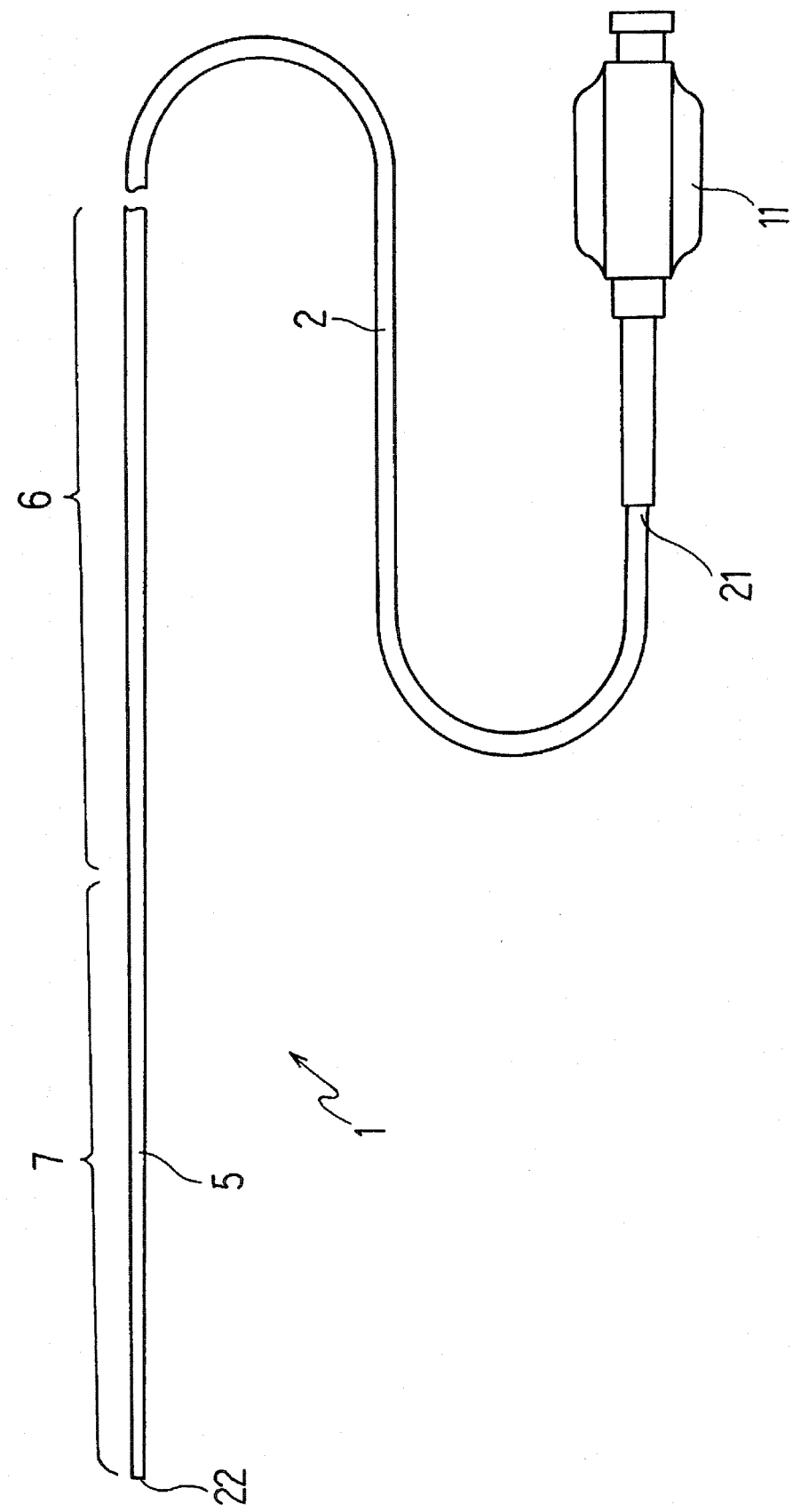
FIG. 1 is a plan view of an embodiment of the vascular catheter of an embodiment of the present invention.
Figure 2:
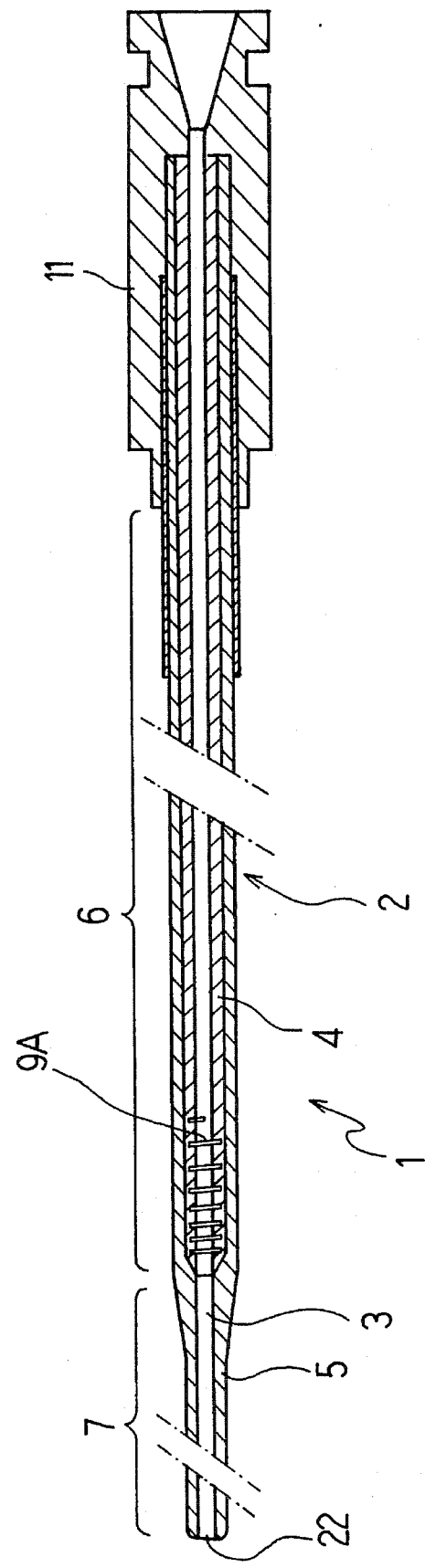
FIG. 2 is a longitudinal sectional view of the vascular catheter shown in FIG. 1.
Figure 3:
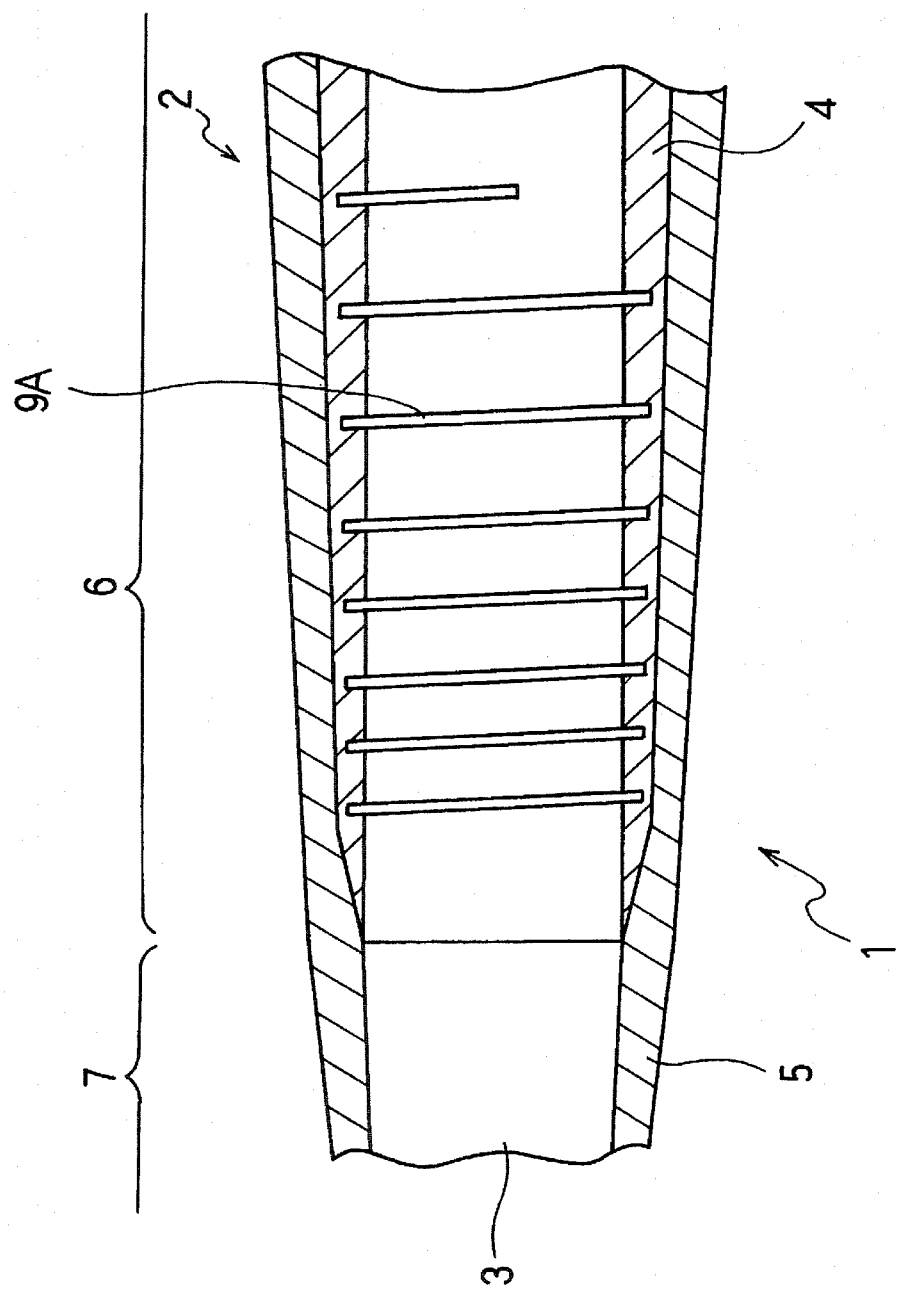
FIG. 3 is an enlarged longitudinal sectional view of the distal end portion of the vascular catheter shown in FIG. 1.

FIG. 1 is a plan view of an embodiment of the vascular catheter of the present invention. FIG. 2 is a partial longitudinal sectional view of the vascular catheter shown in FIG. 1 which shows the proximal and distal end portions of the catheter. FIG. 3 is an enlarged longitudinal sectional view of the distal end portion of the vascular catheter shown in FIG. 1 with the radial dimension enlarged at a larger ratio than the axial dimension in order to show the structure clearly.

The vascular catheter 1 of the present invention comprises a catheter body 2 and a hub 11 attached to the proximal end 21 of the catheter body 2 as shown in FIGS. 1 and 2.

The catheter body 2 has a lumen 3 formed from the proximal end 21 to the distal end 22. When the vascular catheter 1 is inserted into the blood vessel of a patient, a guide wire is passed through the lumen 3. The lumen 3 serves as the conduit for medicine or other liquid after the catheter is inserted. The hub 11 serves as the entrance for a guide wire and the inlet for medicine or other liquid into the lumen 3. The hub 11 is also used as the grip for manipulating the vascular catheter 1.

The catheter body 2 consists of a base or main portion 6 and a tip portion 7. The main portion 6 has a double-tube structure formed by an inner tube 4 and an outer tube 5 closely fitted over and bonded to an outside surface of the inner tube 4. The tip 7 of the catheter is formed by the outer tube 5 alone, that is, by a distal end portion of the outer tube 5 which extends beyond a distal or tip end of the inner tube 4.

In the embodiment shown in FIG. 3, a helical groove 9A is formed in the inside surface of the distal end portion of the inner tube 4 over an appropriate length from the distal end toward the proximal end. Since the wall thickness of the inner tube 4 is thinner at the bottom of the groove 9A and the width of the groove 9A changes (widens or narrows) when the grooved portion is subjected to an external force thereby decreasing the stress in the wall, the entire grooved portion becomes more flexible. Therefore, the bending force applied to the distal end portion of the catheter when the distal end is passed through bends in blood vessel is dispersed into a larger portion (the grooved portion) and kink at the boundary portion between the comparatively rigid main portion 6 of the double-tube structure and the comparatively flexible tip 7 of the single-tube structure caused by the concentration of stress can be prevented.

In the embodiment shown in FIG. 3, the pitch of the groove 9A becomes gradually smaller toward the distal end 22. By thus forming the groove 9A, the flexibility of the catheter body 2 increases gradually toward the distal end 22, and kink at the aforementioned boundary can be prevented with higher reliability. The pitch may be uniform throughout the length of the groove 9A.

The pitch of the helix of the groove 9A is preferably smaller than the outer diameter of the inner tube 4, and more preferably within the range of about ⅔ to ⅕ of the outer diameter of the inner tube 4. If the pitch is greater than the outer diameter of the inner tube 4, bending force is not adequately dispersed, and hence kink can occur at the grooved portion against the purpose. If the pitch is smaller than ⅕ of the outer diameter of the inner tube 4, on the other hand, the durability of the distal end portion of the inner tube 4 noticeably decreases and this portion can rapture or break.

The pitches of groove 9A is preferably that the smaller at the distal end portion of the groove and larger at the proximal end portion, and the pitch more preferably becomes gradually smaller toward the distal end. By thus forming the helical groove 9A, the flexibility of the portion around the distal end of the inner tube 4 increases more smoothly toward the distal end, which allows this portion of the catheter body 2 to bend in smooth curves and thereby improves the manipulability of the catheter.

The pitch is preferably within the range of about 0.1 to 0.5 mm for the distal end portion of the groove 9A and about 0.5 to 2.0 mm for the proximal end portion. The pitch of the middle portion may be an intermediate value between the pitches of both end portions or may become gradually smaller from the pitch of the proximal end portion to that of the distal end portion.

The depth of the groove 9A is preferably equal to or greater than 50 percent of the wall thickness of the inner tube 4 and more preferably equal to or greater than 80 percent of the same. The width of the groove 9A is preferably about 10 to 100 μm and more preferably about 10 to 50 μm taking into consideration the flexibility and the durability, though there is no definite limit.

The length of the grooved portion of the inner tube 4 is preferably within the range of about 5 to 20 times the outer diameter of the inner tube 4 and more preferably within the range of about 10 to 20 times the same.

The groove 9A may be formed from the distal end of the inner tube 4 or from a position at an appropriate distance from the distal end of the inner tube 4 as the groove 9A of the embodiment shown in FIG. 3. The distance between the distal end of the inner tube 4 and that of the groove 9A is preferably about 1.0 mm and more preferably 0.5 mm. The catheter of this embodiment has one groove 9A, but two or more grooves may be formed the distal end portion of the inner tube.

The distal end portion of the inner tube 4 with the groove 9A formed in the inside surface may not be bonded to the inside surface of the outer tube 5. When the distal end portion of the inner tube 4 is not bonded to the to the outer tube 5, the distal end portion of the catheter body 2 has a higher flexibility.

In this embodiment, the inner diameter of the catheter body 2 (diameter of the lumen 3) is substantially uniform throughout the length of the main portion 6. The outer diameter of the catheter body 2, on the other hand, is substantially uniform throughout the almost entire length of the main portion 6 except the distal end portion (an appropriate length of portion from the distal end).

The distal end portion of the main portion 6 and the corresponding distal end portion of the inner tube 4 become gradually thinner in wall thickness to their distal ends so that this portion of the catheter body 2 gradually tapers to the distal end of the main portion 6 as shown in FIG. 3.

Further, in this embodiment, the distal end of the inner tube 4 is formed in a comparatively steep taped and hence the outer diameter and wall thickness of this tapered end become smaller abruptly. As the result, the inner diameter of this portion of the outer tube 5 becomes smaller at the large diminishing rate, while the outer diameter decreases gradually as described above.

The tip portion 7 of the catheter 1 is formed by the distal end portion of the outer tube 5 which extends beyond the distal end of the inner tube 4. The outer diameter of the tip 7 becomes gradually smaller toward the distal as shown in FIG. 1, and the wall thickness of the tip 7 also decreases gently toward the distal end, as shown in FIG. 3.

By thus gently tapering the outside surface of the distal end portion of the main portion 6 and tip 7 toward the distal end along the axis and moreover decreasing the wall thickness of these portions of the inner and outer tubes 4 and 5 so that the diameter of the lumen 3 is substantially uniform or decreases at a smaller diminishing rate to the distal end of the catheter, the vascular catheter of the present invention has the following advantages: the rigidity of the catheter body 2 smoothly decreases to the distal end, and hence kink at the boundary between the tip 7 and the main portion 6 (boundary between the single-tube and double-tube structure portions) can be prevented with higher reliability; no step is formed in the outside surface at the boundary between the tip 7 and the main portion 6, and accordingly the catheter can be easily inserted into blood vessel without being caught by the entrance opening of a catheter guide or exerting excessive stimuli on the blood vessel or causing damage to the wall of the blood vessel; and the lumen 3 has a sufficiently large diameter up to the distal end with no narrowing nor step in the inside surface at the boundary between the single- and double-tube portions, and hence passing of a guide wire through the lumen 3 becomes easier and kink at the boundary is prevented.

The vascular catheter of the present invention is not limited to the structure of the catheter body 2 as described above, particularly as to the shapes of the inner and outer tubes which become smaller at different diminishing rates along the axis of the catheter toward the distal end. For example, the outer diameter of the catheter body 2 may be uniform or may become gradually smaller toward the distal end at a uniform diminishing rate, throughout the length of the catheter body 2.

When the taper 10 is formed at the distal end of the inner tube 4 as shown in FIG. 3, the tapered region is preferably within the range of about 0.5 to 2.0 mm and more preferably within the range of about 0.5 to 1.0 mm along the axis of the catheter body.

There is no particular limitation on the dimensions of the catheter body 2, and the dimensions of the catheter body 2 can be determined so as to be best suited for the purpose of the catheter.

For the vascular catheter used for cerebral blood vessel, for example, the entire length of the catheter body 2 is preferably about 50 to 200 cm and more preferably about 70 to 150 cm. The length of the tip 7 is preferably about 5 to 30 cm and more preferably about 10 to 20 cm.

The outer diameter of the catheter body 2 at the main portion 6 is preferably within the range of about 0.6 to 2.0 mm and more preferably within the range of about 0.7 to 1.2 mm. The outer diameter of the tip 7 is preferably within the range of about 0.3 to 1.0 mm and more preferably within the range of about 0.6 to 0.9 mm.

The inner diameter of the main portion 6 is preferably within the range of about 0.2 to 1.6 mm and more preferably within the range of about 0.3 to 0.9 mm. The inner diameter of the tip 7 is preferably within the range of about 0.2 to 0.7 mm and more preferably within the range of about 0.3 to 0.6 mm.

The wall thickness of the outer tube 5 at the main portion 6 is preferably within the range of about 0.05 to 0.3 mm and more preferably within the range of about 0.05 to 0.2 mm. The wall thickness of the tip 7 is preferably about 0.05 to 0.4 mm and more preferably abut 0.07 to 0.3 mm. The wall thickness of the inner tube 4 is preferably within the range of about 0.05 to 0.5 mm and more preferably within the range of 0.08 to 0.3 mm.

Figure 4:
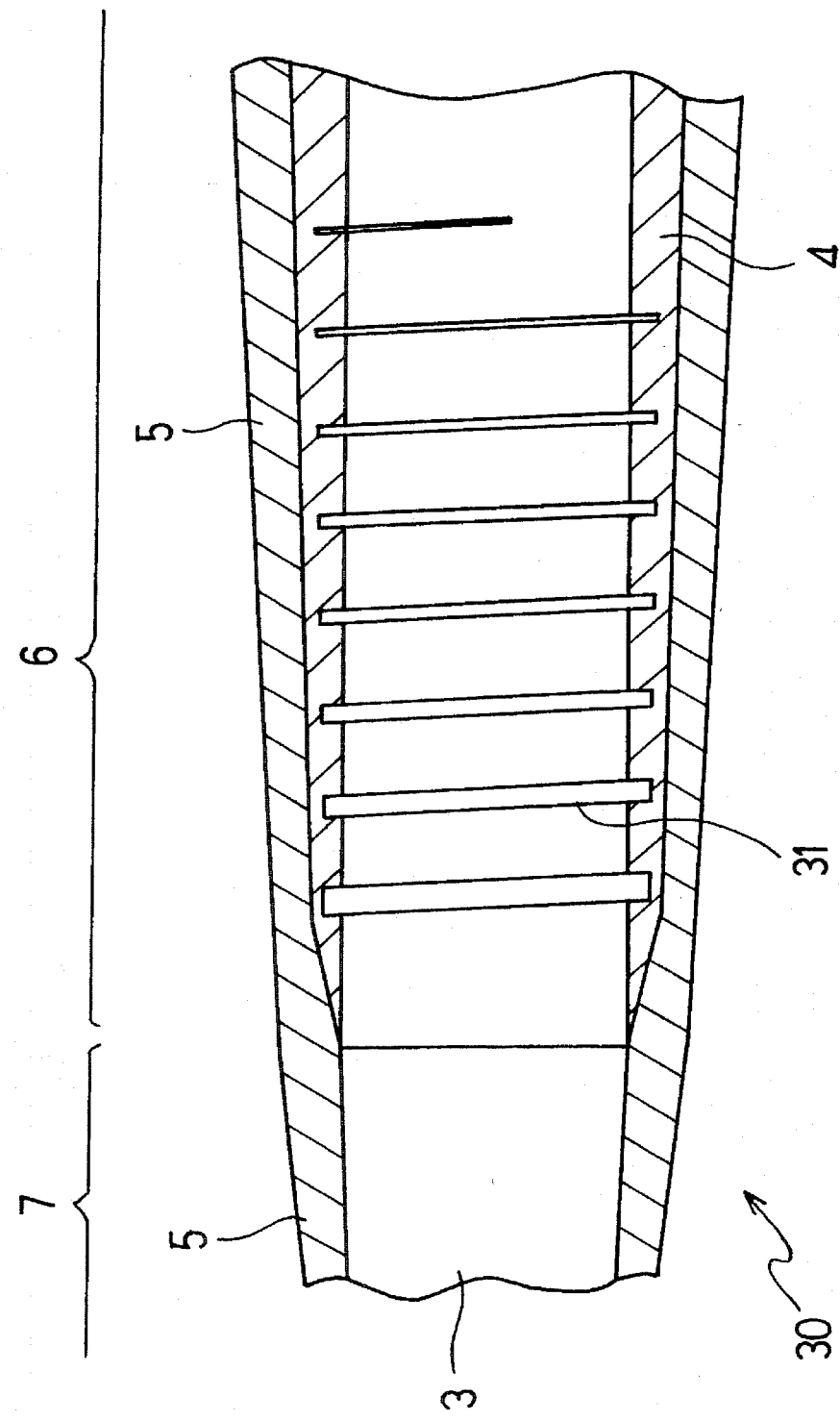
FIG. 4 is an enlarged longitudinal sectional view of the distal end portion of the vascular catheter of another embodiment of the present invention.

The vascular catheter 30 shown in FIG. 4 has another form of the groove in the inner tube. The groove 31 is a helical groove whose width becomes gradually larger toward the distal end. By forming such a helical groove 31, the Flexibility of the portion around the distal end of the inner tube 4 increases more smoothly toward the distal end, which allows this portion of the catheter body 2 to bend in smooth curves and improves the manipulability of the catheter.

The width of the groove 31 is appropriately determined according to the outer diameter of the inner 4. In relation to the outer diameter of the inner tube 4, the width of the groove 31 is preferably within the range of about ½ to 2 times of the outer diameter of the inner tube. For a preferred embodiment, the width of the groove 31 is preferably within the range of about 1.0 to 2.0 mm for the distal end portion of the groove 31 and about 0.1 to 0.5 mm for the proximal end portion. If the width of the groove 31 is within this range, the catheter body 2 has adequate flexibility without breaking of the inner tube 4 during use.

The pitch of the groove 31 is uniform throughout the length of the groove 31. The pitch of the groove 31 may change along the length of the groove and become gradually smaller toward the distal end as that of the groove 9A of the embodiment shown in FIG. 3. The pitch may also become discontinuously smaller toward the distal end.

The inner tube 4 is preferably formed of a comparatively rigid synthetic resin material. The material usable for the inner tube 4 includes synthetic resins such as polyolefin (polyethylene, polypropylene, ethylene-vinyl acetate copolymer, etc.), polyamide, polyester (polyethylene-terephthalate, polybutylene-terephthalate, etc.), poly(vinyl chloride), polyurethane, polystyrene resin, fluororesin (polytetrafluoroethylene, etc.) and polyimide, and synthetic resin elastomers such as silicone rubber, polyamide elastomer, polyester elastomer, poly(vinyl chloride) elastomer and polyurethane elastomer. Of these materials, elastomers are preferable, and especially polyamide elastomer and polyester elastomer are preferable.

By using at least one of these materials, the inner tube 4 with appropriate flexural elasticity and high solvent resistance is prepared.

When an elastomer is used, the inner tube 4 expands or contracts elastically as a spring in the direction of the axis and thereby increases the flexural elasticity of the catheter body 2. The catheter body 2, with the increased flexural elasticity, can bend more easily in smooth curves along blood vessel, and kink at the boundary between the single- and double-tube portions is prevented with higher reliability.

Further, polyamide elastomer and polyester elastomer have comparatively high rigidity at around room temperature giving the catheter body 2 higher pushability and turnability, and become flexible at around body temperature giving catheter body 2 higher flexibility and hence improved pliability and reluctance to kinking after the catheter is inserted in the body of a patient.

A typical polyamide elastomer is block copolymer of nylon 6, nylon 64, nylon 66, nylon 610, nylon 612, nylon 46, nylon 9, nylon 11, nylon 12, N-alkoxymethyl modified nylon, or aliphatic or aromatic polyamide (hexamethylene-diamineisopthalic acid condensation polymer, metaxloil-diamineadipic acid condensation polymer, etc.) as the hard segment and a polymer such as polyester or polyether as the soft segment. Further, polyamide elastomer here includes a polymer alloy (polymer blend, graft polymer and random polymer) of the above-mentioned polyamide elastomer and one or more soft resins, the above-mentioned polyamide softened with a plasticizer, and a mixture of them. For the plasticizer, one difficult to be extracted with solvents or blood is preferable.

A typical polyester elastomer is block copolymer of saturated polyester (polyethylene-terephthalate, polybutylene-terephthalate, etc.) and polyester or polyether. Further, polyester elastomer here includes a polymer alloy of the above-mentioned polyester elastomer and one or more soft resins, the above-mentioned polyester softened with a plasticizer, and a mixture of them.

Various additives such as alloying agent, compatibilizer, hardening agent, softening agent, stabilizer and coloring agent may be added to the above-mentioned elastomers if necessary.

A thermoplastic elastomer is preferable, because forming of the inner tube 4 is easier.

The inner tube 4 is normally formed of a uniform material for the whole, but may be formed of different materials for appropriately determined portions.

The outer tube 5 is preferably formed of a comparatively soft synthetic resin material than the synthetic resin material of the inner tube 4. The outer tube 5 is preferably more soft than the inner tube 4.

The resin material usable for the outer tube 5 includes synthetic resins such as polyolefin (polyethylene (especially low density polyethylene), polypropylene, ethylene-vinyl acetate copolymer, etc.), polyamide, polyester (polyethylene-terephthalate, polybutyleneterephthalate, etc.), polyurethane, polystyrene resin, fluororesin (polytetrafluoroethylene, etc.) and polyimide, and synthetic resin elastomers such as above-mentioned polyamide elastomer, above-mentioned polyester elastomer, polyurethane elastomer, poly(vinyl chloride) elastomer, polystyrene elastomer, fluoroelastomer, silicone rubber and latex robber.

In these materials, elastomers are preferable, and especially polyamide elastomer and polyester elastomer are preferable. The most preferable elastomer is polyester elastomer.

A thermoplastic elastomer is preferable, because forming of the outer tube 5 is easier.

By using at least one of these materials, the outer tube 5 with softness, appropriate flexural elasticity and high solvent resistance is prepared.

The outer tube 5 is normally formed of a uniform material for the whole, but may be formed of different materials for appropriately determined portions.

The rigidity (buckling strength) (ASTM D-790, at 23° C.) of the material for the inner tube 4 is preferably within the range of 1,500 to 15,000 $kg/cm^2$ and more preferably 2,000 to 8,000 $kg/cm^2$. If the buckling strength of the material is less than 1,500 $kg/cm^2$, the catheter body 2 is too flexible to convey pushing force in the direction of the axis and turning force around the axis from the proximal portion to the distal end 22. On the other hand, if the buckling strength is greater than 15,000 $kg/cm^2$, the catheter body 2 is too rigid to bend flexibly along the guide wire and exerts excessive force on the wall of blood vessel. Further, the difference between the rigidity of the single-tube and double-tube portions increases and the reluctance to kinking at the boundary portion becomes too low.

The rigidity (buckling strength) (ASTM D-790, at 23° C.) of the material for the outer tube 5 is preferably within the range of 5 to 1,500 $kg/cm^2$ and more preferably 300 to 800 $kg/cm^2$. If the buckling strength of the material is less than 5 $kg/cm^2$, the catheter body 2 is too flexible to convey pushing force in the direction of the axis and turning force around the axis from the proximal portion to the distal end 22. Further, the difference between the rigidity of the single- and double-tube portions increases and the reluctance to kinking at the boundary becomes too low.

The difference between the rigidity (buckling strength) (ASTM D-790, at 23° C.) of the materials for the inner and outer tubes 4 and 5 is preferably within the range of 100 to 14,000 $kg/cm^2$ and more preferably 100 to 3,000 $kg/cm^2$.

In the catheter of this embodiment, substantially entire outside surface of the inner tube 4 is in close contact with and bonded to the inside surface of the outer tube 5. The methods usable for bonding the inner tube 4 and the outer tube 5 are adhering with an adhesive or solvent, welding by heating, and inserting the inner tube 4 into the outer tube 5 swollen with a solvent, for example. Although the inner tube 4 is entirely bonded to the outer tube 5 in this embodiment, the distal end portion (grooved portion) of the inner tube 4 may not be bonded to the outer tube 5. The method for bonding the inner tube 4 and the outer tube 5 without bonding the distal end portion of the inner tube 4 is subjecting the inner and outer tubes 4 and 5 to the bonding process after applying to the distal end portion of the inner tube 4 an appropriate substance (such as silicone, for example silicone oil) which prevents the tubes from bonding together.

The outside surface of the catheter body 2 is preferably coated with a hydrophilic (or water soluble) high-molecular substance. The hydrophilic substance becomes lubricous and decreases the coefficient of friction between the catheter body 2 and blood vessel when it comes into contact with blood or physiologic saline, significantly increasing the easiness of insertion, flexibility to bend along a guide wire or blood vessel, reluctance to kink of the catheter body 2.

For the hydrophilic high-molecular substance for this purpose, the following natural and synthetic high-molecular substances and their derivatives can be used.

<Natural High-Molecular Substance>
1. Starch related substance

Example: Carboxymethyl starch, Dialdehyde starch
2. Cellulose related substance

Example: CMC (Carboxymethyl cellulose), MC (Methyl cellulose), HEC (hydroxyethyl cellulose), HPC (hydroxypropyl cellulose)
3. Tannin and lignin and related substance Example: Tannin, Lignin
4. Polysaccharide related substance Example: Alginic acid, Gum arabic, Gua gum, Tragacanth gum
5. Protein Example: Gelatin, Casein, Glue, Collagen <Synthetic Water-Soluble High-Molecular Substance>
1. PVA related substance Example: Poly(vinyl alcohol)
2. Polyethylene oxide related substance Example: Polyethylene oxide, Polyethylene glycol
3. Acrylic acid related substance Example: Polyacrylic acid soda
4. Maleic anhydride related substance Example: Methyl vinyl ether-maleic anhydride copolymer
5. Phthalic acid related substance Example: Polyhydroxyethyl-phthalic acid ester
6. Water-soluble polyester Example: Polydimethylol-propionic acid ester
7. Ketone aldehyde resin Example: Methylisopropylketone-formaldehyde resin 8. Acrylamide Example: Polyacrylamide
9. PVP Example: Poly(vinyl pyrrolidone)
10. Polyamine Example: Polyethyleneimine
11. Polyelectrolyte Example: Polystyrene sulfonate
12. Others Example: Water-soluble nylon Of the above substances, cellulose-derived high-molecular substance (hydroxypropyl cellulose, for example), polyethylene oxide-derived high-molecular substance (polyethylene glycol, for example), maleic anhydride-derived high-molecular substance (maleic anhydride copolymer such as methyl vinyl ether-maleic anhydride copolymer), acrylamide-derived high-molecular substance (polyacrylamide, for example), water-soluble nylon (AQ-nylon P-70 from Toray, for example) are preferable, because a small coefficient of friction is obtained stably.

Derivatives of the above high-molecule substances usable for this friction reduction are not limited to water-soluble derivatives only and may be insoluble derivatives which have each of the above hydrophilic high-molecule substances as their basic structure and a degree of freedom in molecular chains to contain combined water.

Therefore, derivatives usable for the friction reduction include ester, salt, amide, anhydride, halide, ether, hydrolysate, acetal, formal, alkylol, quaternary compound, diazo hydrazide, sulfonated compound, nitro and ion complex obtained by condensation, addition, substitution, oxidation and reduction reaction, compound produced by cross-linking with substances which have more than two reactive functional groups such as diazonium group, azido group, isocyanate group, acid chloride group, acid anhydride group, imino carbonate group, amino group, carboxyl group, epoxy group, hydroxyl group and aldehyde group, vinyl compound, and compound obtained by copolymerization with acrylic acid, methacrylic acid, diene compound and maleic anhydride.

The coating of such a hydrophilic high-molecular substance is preferably fixed to the outside surface of the catheter body 2 by bonding the high-molecular substance with the reactive functional group which exists or is introduced in the catheter body 2 or on the surface of the catheter body 2 by covalent bond. By thus fixing the coating of a hydrophilic high-molecular substance to the outside surface of the catheter body 2, a durable lubricous surface is obtained.

The reactive functional group which exist or is introduced in the catheter body 2 or on the surface of the catheter body 2 may be any group which reacts with the high-molecular substance to bond or cross link, such as diazonium group, azido group, isocyanate group, acid chloride group, acid anhydride group, imino carbonate group, amino group, carboxyl group, epoxy group, hydroxyl group and aldehyde group. Isocyanate group, amino group, epoxy group and hydroxyl group are preferable.

The average molecular weight of the hydrophilic high-molecular substance used for the friction reduction is preferably within the range of 30,000 to 50,000, though there is no particular limit. By using a hydrophilic high-molecular substance of an average molecular weight within this range, a lubricous coating with a high lubricity, a preferable thickness, and a preferable degree of swelling when containing water can be formed.

The thickness of the lubricous coating is preferably within the range of 0.1 to 100 µm and more preferably 1 to to 30 µm, though there is no particular limit.

For the composition of the hydrophilic high-molecular substance used and the method for forming the coating, those disclosed by Japanese patent application laid open under Provisional Publication No. 106778/1978, U.S. Pat. No. 4100309, Japanese patent application laid open under Provisional Publication No. 259269/1985, and Japanese patent application published under Publication No. 33181/1989 can be used.

Figure 5:
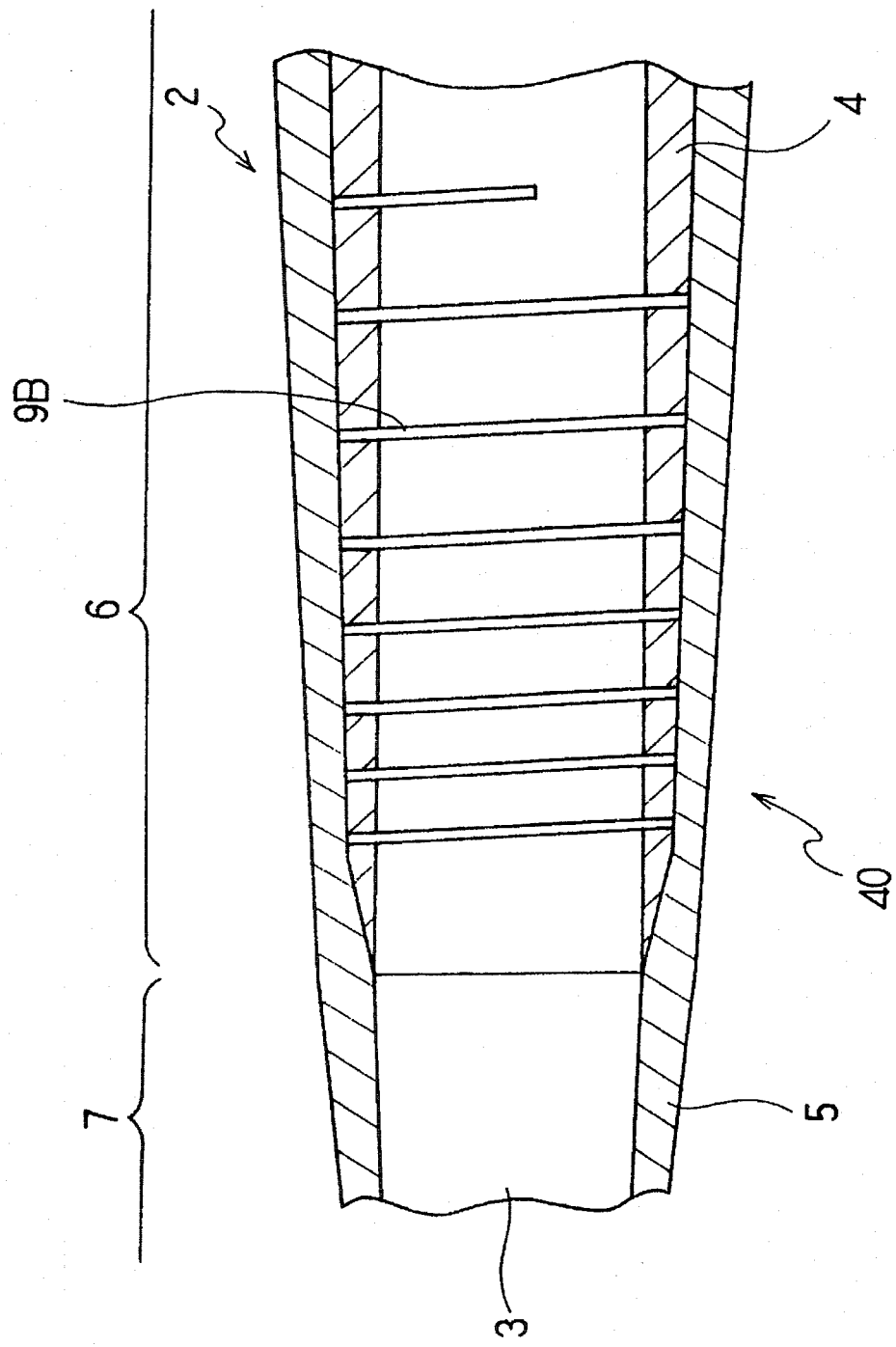
FIG. 5 is an enlarged longitudinal sectional view of the distal end portion of the vascular catheter of another embodiment of the present invention.

Next, the vascular catheter of the embodiment shown in FIG. 5 is described.

Figure 6:
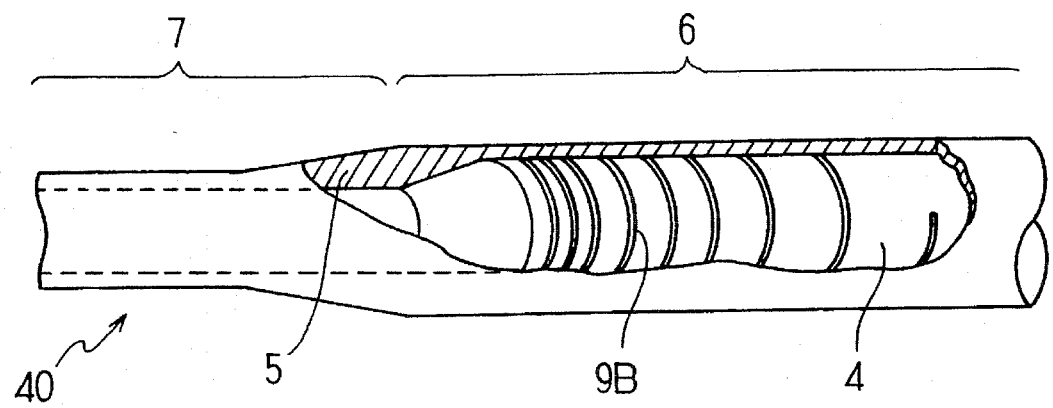
FIG. 6 is a partially broken external view of the distal end portion of the catheter shown in FIG. 5.

FIG. 5 is an enlarged cross-sectional view of the distal end portion of the vascular catheter of another embodiment of the present invention. FIG. 6 is a partially broken external view of the distal end portion of the vascular catheter shown in FIG. 5. The same parts as those of the catheter shown in FIG. 3 are designated by the same numerals and the description of them is omitted.

The catheter 40 has almost the same structure as the catheter 1 shown in FIG. 3. The difference between their structures is that the catheter 40 has a helical slit or slot 9B instead of the helical groove 9A of the catheter 1. The helical slot 9B is-formed through the wall of the inner tube 4 from the inside surface to the outside surface. Since the width of the slot 9B can change more easily than that of the groove 9A, the flexibility of the portion provided with the helical slot 9B is greater than that of the portion provided with the helical groove 9A as shown in FIG. 3, though the strength becomes smaller.

The width of the helical slot 9B of the catheter 40 of this embodiment is appropriately determined by taking into account the outer diameter of the inner tubes 4. It is preferably within the range of about ⅕ to 2 times of the outer diameter of the inner tube 4. For a preferred embodiment, the width of the slot 9B is preferably within the range of about 0.1 to 2.0 mm. If the width of the slot 9B is within this range, the catheter has adequate flexibility without occurrence of breaking of the inner tube 4 during use.

The pitch of the slot 9B becomes gradually smaller toward the distal end as shown in FIGS. 5 and 6. The pitch of the slot 9B may become discontinuously smaller toward the distal end.

Figure 7:
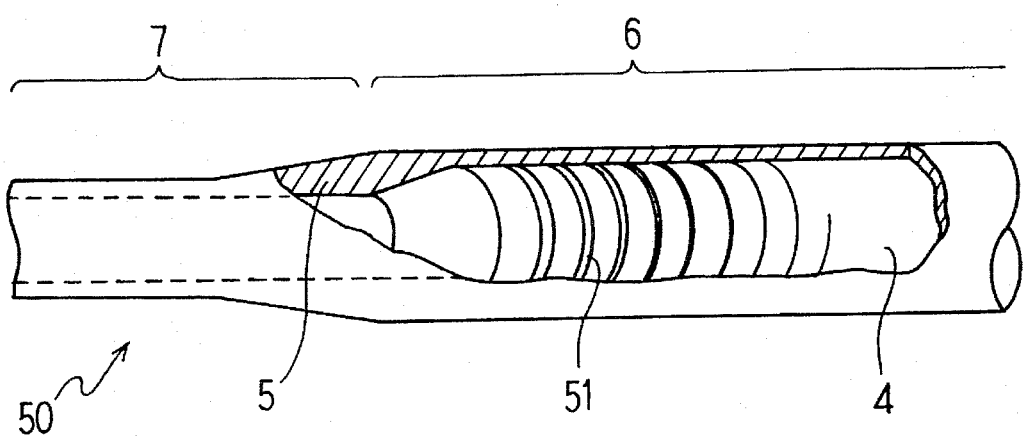
FIG. 7 is a partially broken external view of the distal end portion of the vascular catheter of another embodiment of the present invention.

The slot may also have the shape as that of the slot 51 of the catheter 50 shown in FIG. 7. In this embodiment, the width of the slot 51 is greater at the distal end portion of the slot 51 and smaller at the proximal end portion. By forming the slot in this shape, the flexibility of the portion provided with the slot increases gradually toward the distal end, and hence the portion around the distal end of the inner tube 4 bend more easily in smooth curves to improve the manipulability of the catheter.

The width of the helical slot 51 of the catheter 50 is determined by taking into account the diameter of the inner tube 4 and other factors. The width of the slot is preferably within the range of about ½ to 2 times of the outer diameter of the inner tube 4. For a preferred embodiment, the width of the slot 51 is preferably within the range of about 1.0 to 2.0 mm for the distal end portion and within the range of about 0.1 to 0.5 mm for the the proximal end portion. If the width of the slot is within this range, the catheter has adequate flexibility and there is no occurrence of breaking of the inner tube 4 during use.

The pitch of the slot 51 is uniform throughout the length of the slot. The pitch of the slot 51 may become gradually smaller toward the distal end as that of the slot 41 of the embodiment shown in FIG. 6 or may become discontinuously smaller toward the distal end. The catheters 40 and 50 has one slot 41 or 51, but two or more slot may be formed the distal end portion of the inner tube.

Figure 8:
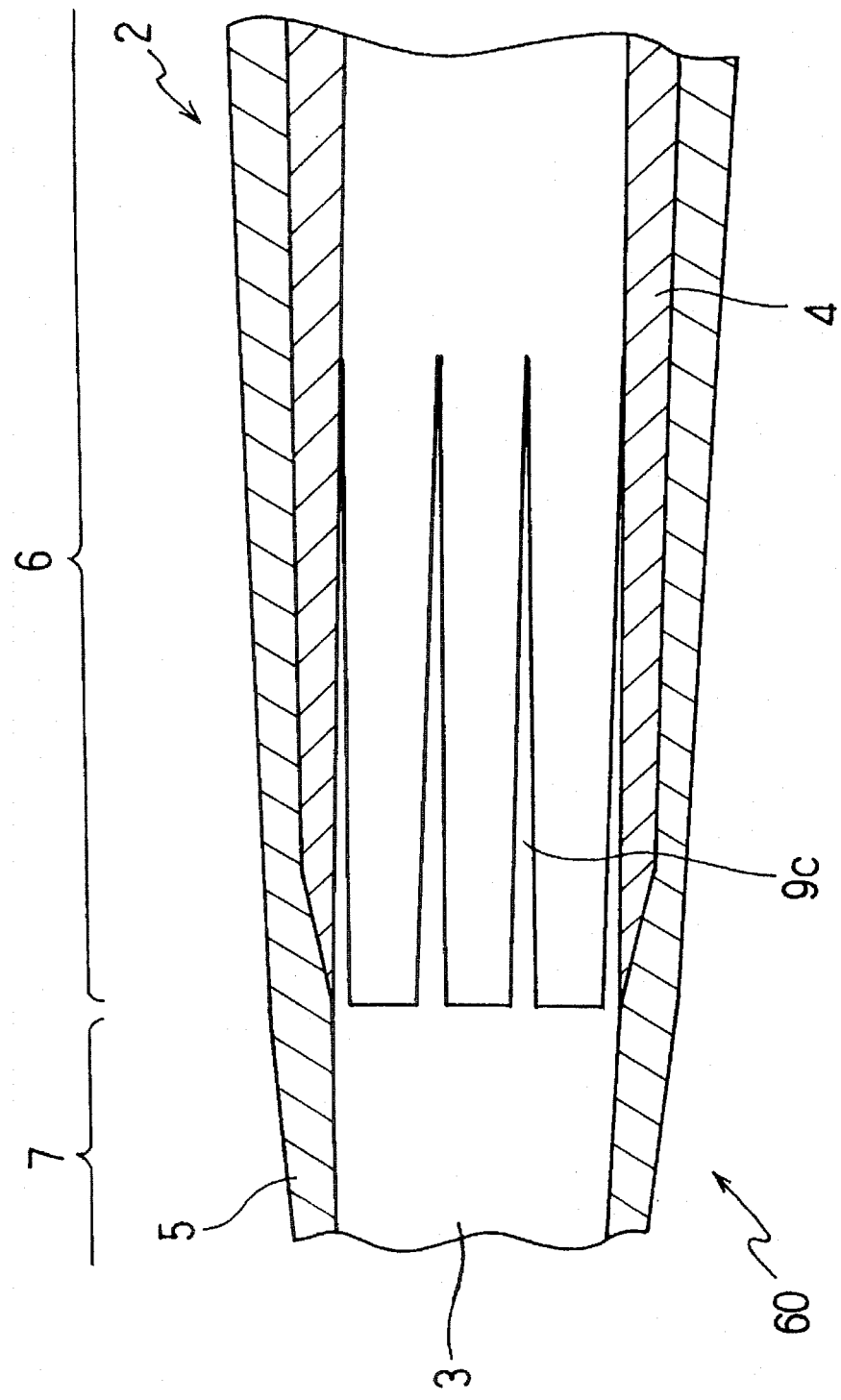
FIG. 8 is an enlarged longitudinal sectional view of the distal end portion of the vascular catheter of another embodiment of the present invention.

Next, the vascular catheter of the embodiment shown in FIG. 8 is described.

Figure 9:
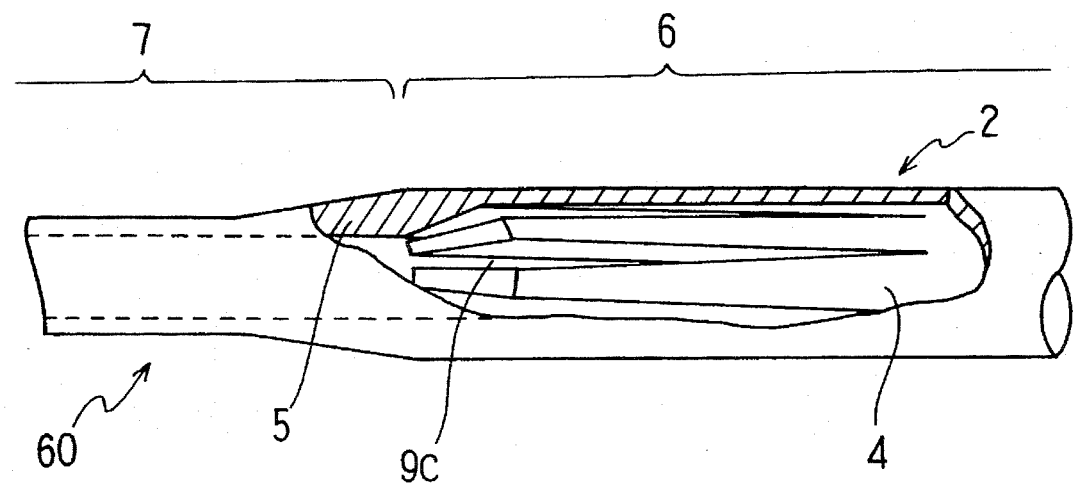
FIG. 9 is a partially broken external view of the distal end portion of the catheter shown in FIG. 8.

FIG. 8 is an enlarged longitudinal sectional view showing the structure of the distal end portion of another embodiment of the vascular catheter of present invention. FIG. 9 is a partially broken external view of the distal end portion of the vascular catheter shown in FIG. 8. The same parts as those of the catheter shown in FIG. 3 are designated by the same numerals and the description of them is omitted.

The vascular catheter 60 has almost the same structure as the catheter 1 shown in FIG. 3. The difference between their structures is that the catheter 60 has a plurality of slits 9C which extend from the distal end of the inner tube 4 toward the proximal end substantially in parallel to the axis instead of the helical groove 9A of the catheter 1.

The width of the slits 9C changes (widens or narrows) when the portion having the slits is subjected to an external force thereby decreasing the stress in the wall, the entire portion having the slits becomes more flexible. Therefore, the bending force applied to the distal end portion of the catheter when the distal end is passed through bends in blood vessel is dispersed into a larger portion (the portion having the slits) and kink at the boundary portion between the comparatively rigid main portion 6 of the double-tube structure and the comparatively flexible tip 7 of the single-tube structure caused by the concentration of stress can be prevented.

It may be uniform throughout the length of the slits, but the width of the slits 9C becomes gradually smaller toward the proximal end as shown in FIG. 8.

There is no particular limit to the width of the slits 9C, but the width is preferably within the range of about 0.2 to 1.0 mm and more preferably within about 0.3 to 0.7 mm for the slits 9C of a uniform width, and preferably within the range of about 0.3 to 1.0 mm and more preferably within about 0.7 to 1.0 mm at the distal end for the slits 9C of a tapered width.

The number of the slits 9C is preferably within the range of about 3 to 8. The slits 9C are formed at equal spaces in the circumference of the inner tube 4.

Longitudinal grooves (depressions) in the direction of the axis may be used instead of the slits 9C. The longitudinal grooves may be formed in either side surface of the inner tube 4.

The helical groove 9A may be formed in either side surface of the inner tube 4. The depth of the longitudinal grooves is preferably within the same range as the preferable range for the helical groove 9A of the embodiment shown in FIG. 3.

Although the present invention is described above with reference to the embodiments shown in the drawings, the present invention is not limited to the structures of those embodiments and includes various modifications and variations. For example, the distal end portion of the inner tube 4 may be made of a material more elastic than that of the other portion of the inner tube 4 in order to increase the flexibility of that portion of the inner tube 4.

Further, the groove, slot or slit in the inner tube 4 may be filled with the resin material of the outer tube 5, though it is preferable that they are substantially left unfilled, more preferable that they make spaces. The groove, slot or slit of the inner tube forms a space in the inner tube as shown in Figures.

Next, examples of the vascular catheter of present invention are described below in detail.

EXAMPLE 1

A tubing for the inner tube 4 was formed of a polyamide elastomer which is copolymer of polytetramethyleneglycol and nylon 12 (Product Name Pebax 7033, Toray Corporation, Buckling strength: 4390 kg/cm$^2$ (ASTM D-790 at 23° C.)). The outer tube 5 was formed of a polyester elastomer which is copolymer of polytetramethyleneoxide and polybutyleneterephthalate (Product Name Hytrel 4077, Toray corporation, Buckling strength: 720 kg/cm$^2$ (ASTM D-790 at 23° C.)).

One end portion of the tubing for the inner tube 4 was heated and drawn into a tapered shape with the outer diameter becoming gradually smaller toward the end.

The end portion of this tapered portion was put over a screw having a projecting helical rib and heated from the outside, and the screw was pulled off. Thus a helical groove 9A extending in the direction of the axis was formed in the inside surface of the inner tube 4.

The groove 9A was 0.35 mm in width and 0.06 mm in depth on average. The beginning end of the groove 9A was 1.0 mm from the distal end (the end of the tapered portion) of the inner tube 4. The length of the grooved portion was 10 mm. The pitch of the helix was 0.30 mm at the most distal side and 0.60 mm at the most proximal side and became gradually smaller toward the distal end.

The inner tube 4 prepared as above was inserted into the outer tube 5, and both tubes were bonded together by heating. Thus a catheter body 2 of the structure as shown in FIG. 3 was made.

Finally, a hub 11 was attached to the proximal end 21 of the catheter body 2, and the first example of the vascular catheter of the present invention was made.

The dimensions of the catheter body 2 were as follows.

Overall length of the catheter body: 150 cm

Length of the main portion: 130 cm

Length of the tip portion: 20 cm

Outer diameter of the catheter body:
  From the proximal end to 120 cm: 1.1 mm
  From 120 cm to 130 cm: Gradually decreases from 1.1 mm to 1.0 mm.
  From 130 cm to the tip end: Gradually decreases from 1.0 to 0.75 mm.

Inner diameter of the catheter body:
  Main portion: 0.65 mm
  Tip portion: Gradually decreases from 0.65 mm to 0.55 mm Wall thickness of the inner tube:
  From the proximal end to 120 cm: 0.14 mm
  From 120 cm to 129.9 cm: Gradually decreases from 0.14 mm to 0.08 mm.
  From 129.9 cm to the tip end: Decreases from 0.08 to 0 mm.

EXAMPLE 2

Another catheter body of the vascular catheter of the present invention was made in the same manner as example 1, except that a helical slot as shown in FIG. 5 instead of the helical groove was formed. Finally, a hub 11 was attached to the proximal end 21 of the catheter body 2, and the second example of the vascular catheter of the present invention was made.

The helical slot was 0.35 mm in width on the average. The beginning end of the slot was 1.0 mm from the distal end of the inner tube 4. The length along the axis of the portion provided with the helical slot was 10 mm. The pitch of the helix was 0.30 mm at the most distal side and 0.60 mm at the most proximal side and became gradually smaller toward the distal end.

EXAMPLE 3

Another catheter body of the vascular catheter of the present invention was made in the same manner as in example 1, except that slits as shown in FIG. 8 instead of the helical groove were formed. Finally, a hub 11 was attached to the proximal end 21 of the catheter body 2, and the third example of the vascular catheter of the present invention was made.

The slits 9C were 5 mm in length in the direction of the axis and became gradually wider to the distal end of the inner tube 4. The width of the slits were 0.08 mm at the proximal end and 0.2 mm at the proximal end. Six slits were formed at equal spaces in the circumference of the inner tube 4.

EXAMPLE 4

The fourth example of the vascular catheter of the present invention was made in the same manner as in example 1, except that longitudinal grooves (depressions in the direction of the axis) instead of the helical groove were formed in the inside surface of the inner tube 4.

The depth of the grooves were 0.06 mm on average.

Comparison Example

A vascular catheter for comparison was made in the same manner as in example 1, except that no groove was formed in the inner tube.

Test

The vascular catheters of examples 1 to 4 and the comparison example were subjected to the following bending test to examine the reluctance to kink at the boundary between the single-tube and double-tube structures.

The boundary portion of the catheter body of each catheter was pressed around cylinders of different outer diameters in water at 37° C. to bend at the curvature of the each cylinder, and the diameter of the cylinder when folds occurred in the catheter body was measured (the measurement was repeated 5 times).

The test result is shown in Table 1.

TABLE I

| | Folds Occurred in Catheter Body |
|---|---|
| Example 1 | 5.0 mm |
| Example 2 | 4.5 mm |
| Example 3 | 5.5 mm |
| Example 4 | 5.7 mm |
| Com. Ex. | 7.0 mm |

It is known from Table 1 that the vascular catheters of the present invention of examples 1 to 4 endure bending of greater curvature than the catheter of the comparison example and have a higher reluctance to kink.

As described above, the vascular catheter of this invention can bend more easily along a guide wire and blood vessels than conventional catheters because of the structure of the catheter body having the proximal main portion made up of double tubes and the distal tip made up of a single tube and the higher flexibility of the distal end portion of the inner tube increased by a helical groove, a helical slot or helical slit, longitudinal slits, longitudinal groove. The vascular catheter of this invention hence has a higher reluctance to kicking, exerts smaller stimuli on blood vessels, causes less damage to the wall of blood vessels, improved manipulability, and higher safety than conventional catheters.

I claim:

1. A vascular catheter comprising a flexible slender catheter body which is made up of an inner tube formed of a synthetic resin and an outer tube formed of a synthetic resin covering the outside surface of the inner tube and having a main portion, tip portion and a lumen, wherein said main portion of said catheter body is made up of said inner tube and said outer tube, said tip of said catheter body is made up of a portion of said outer tube which extends from a distal end of said inner tube, and said inner tube has at least one helical space contained in a distal portion of said inner tube, and wherein said distal portion having said helical space exhibits gradually increasing flexibility from a proximal end to a distal end of said distal portion which contains the helical space.

2. The vascular catheter of claim 1, wherein the width of said helical space changes when a portion of said catheter comprising said helical space is subjected to an external force.

3. A vascular catheter of claim 1, wherein said helical space is formed by a helical groove contained in said inner tube.

4. A vascular catheter of claim 1, wherein said helical space is formed by a helical slit contained in said inner tube.

5. A vascular catheter of claim 1, wherein said outer tube is formed of a synthetic resin which is softer than the synthetic resin which forms said inner tube.

6. A vascular catheter of claim 1, wherein said synthetic resin which constitutes both or either one of said inner and outer tubes is a synthetic resin elastomer.

7. A vascular catheter of claim 1, wherein the pitch of said helical space gradually decreases toward the distal end.

8. A vascular catheter of claim 1, wherein the width of said helical space gradually increases toward the distal end.

9. A vascular catheter of claim 1, wherein said catheter is suitable for use in accessing a brain blood vessel.

10. The vascular catheter of claim 1, wherein said helical space extends from a distal end of said inner tube to an appropriate position in the same direction as an axis of said inner tube.

11. The vascular catheter of claim 1, wherein said helical space extends from about a distal end of said inner tube to an appropriate position in the same direction as an axis of said inner tube.

12. The vascular catheter of claim 1, wherein the pitch of said helical space gradually decreases toward the distal end of said inner tube and the width of said helical space gradually increases toward the distal end of said inner tube.

13. The vascular catheter of claim 1, wherein the pitch of said helical space is smaller at the distal end portion of said helical space and larger at the proximal end portion of said helical space.

14. The vascular catheter of claim 1, wherein the pitch of said helical space is smaller at the distal end portion of said helical space and larger at the proximal end portion of said helical space, and the pitch of a middle portion of said helical space is an intermediate value relative to the pitches of both end portions of said helical space.

15. A vascular catheter comprising a flexible slender catheter body which is made up of an inner tube formed of a synthetic resin and an outer tube formed of a synthetic resin covering the outside surface of the inner tube and having a main portion, tip portion and a lumen, wherein
said main portion of said catheter body is made up of said inner tube and said outer tube,
said tip of said catheter body is made up of a portion of said outer tube which extends from a distal end of said inner tube, and
said inner tube has at least one helical space contained in a distal portion of said inner tube, and wherein a proximal portion of said inner tube does not contain said helical space.

16. The vascular catheter of claim 15, wherein said distal portion of said inner tube exhibits gradually increasing flexibility from a proximal end to a distal end of said distal portion comprising said helical space.

17. The vascular catheter of claim 16, wherein said outer tube is formed of a synthetic resin which is softer than the synthetic resin which forms said inner tube.

18. The vascular catheter of claim 15, wherein the width of said helical space changes when a portion of said catheter comprising said helical space is subjected to an external force.

19. The vascular catheter of claim 15, wherein said helical space is formed by a helical groove contained in said inner tube.

20. The vascular catheter of claim 15, wherein said helical space is formed by a helical slit contained in said inner tube.

21. The vascular catheter of claim 15, wherein said synthetic resin which constitutes either or both of said inner and outer tubes is a synthetic resin elastomer.

22. The vascular catheter of claim 15, wherein the pitch of said helical space gradually decreases toward the distal end.

23. The vascular catheter of claim 15, wherein the width of said helical space gradually increases toward the distal end.

24. The vascular catheter of claim 15, wherein said catheter is suitable for use in accessing a brain blood vessel.

25. The vascular catheter of claim 15, wherein said helical space extends from a distal end to an appropriate position in the same direction as an axis of said inner tube.

26. The vascular catheter of claim 15, wherein said helical space extends from about the distal end to an appropriate position in the same direction as an axis of said inner tube.

27. The vascular catheter of claim 15, wherein the pitch of said helical space gradually decreases toward the distal end and the width of said helical space gradually increases toward the distal end.

28. The vascular catheter of claim 15, wherein the pitch of said helical space is smaller at the distal end portion of said helical space and larger at the proximal end portion of said helical space.

29. The vascular catheter of claim 15, wherein the pitch of said helical space is smaller at the distal end portion of said helical space and larger at the proximal end portion of said helical space, and the pitch of a middle portion of said helical space comprises an intermediate value relative to the pitches of both end portions of said helical space.

* * * * *

UNITED STATES PATENT AND TRADEMARK OFFICE
CERTIFICATE OF CORRECTION

PATENT NO. : 5,531,719
DATED : July 2, 1996
INVENTOR(S) : Tohru TAKAHASHI

It is certified that error appears in the above-indentified patent and that said Letters Patent is hereby corrected as shown below:

In Column 4, line 53, delete "taped" and insert -- taper --.

In Column 6, line 2, delete "Flexibility" and insert -- flexibility --.

Signed and Sealed this

Fifth Day of November, 1996

Attest:

BRUCE LEHMAN

*Attesting Officer*   *Commissioner of Patents and Trademarks*